US008589827B2

(12) United States Patent
Biafore et al.

(10) Patent No.: US 8,589,827 B2
(45) Date of Patent: Nov. 19, 2013

(54) PHOTORESIST SIMULATION

(75) Inventors: John J. Biafore, North Scituate, RI (US); Mark D. Smith, Austin, TX (US); John S. Graves, III, Austin, TX (US); David Blankenship, Austin, TX (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 12/915,455

(22) Filed: Oct. 29, 2010

(65) Prior Publication Data

US 2011/0112809 A1      May 12, 2011

Related U.S. Application Data

(60) Provisional application No. 61/260,533, filed on Nov. 12, 2009.

(51) Int. Cl.
*G06F 17/50* (2006.01)
*G06F 17/10* (2006.01)
*G06F 7/60* (2006.01)
*G06G 7/62* (2006.01)
*G06G 7/58* (2006.01)
*G06G 7/48* (2006.01)

(52) U.S. Cl.
USPC ......... 716/51; 716/54; 703/2; 703/12; 703/13

(58) Field of Classification Search
None
See application file for complete search history.

(56) References Cited

U.S. PATENT DOCUMENTS 6,081,659 A    6/2000  Garza
8,108,805 B2 *  1/2012  Rathsack ........................ 716/52

2003/0044703 A1   3/2003  Yamada
2007/0196747 A1   8/2007  Granik
2008/0243730 A1  10/2008  Bischoff et al.

OTHER PUBLICATIONS

Rathsack et al., Resist fundamentals for resolution, LER and sensitivity (RLS) performance tradeoffs and their relation to microbridgins defects, Proceedings of the SPIE, vol. 7273, pp. 727347-727347-11 (Mar. 2009).*
Gallatin et al., Resolution, LER and Sensitivity Limitations of Photoresist, Proceedings of the SPIE, vol. 6921, pp. 69211E-1-69211E-11 (2008).*
Gallatin et al., Powerpoint presentation on Resolution, LER, and Sensitivity Limitations of Photoresist, Advanced Materials Research Center, 21 pages, Oct. 2007.*
Brainard et al., Photons, Electrons, and Acid Yields in EUV Photoresists: A progress report, Proceedings of the SPIE, vol. 6923, pp. 692325-1-692325-14 (2008).*

* cited by examiner

*Primary Examiner* — A. M. Thompson
(74) *Attorney, Agent, or Firm* — Luedeka Neely Group, P.C.; Rick Barnes

(57) ABSTRACT

A processor based method for measuring dimensional properties of a photoresist profile. A number acid generators and quenchers within a photoresist volume is determined. A number of photons absorbed by the photoresist volume is determined. A number of the acid generators converted to acid is determined. A number of acid and quencher reactions within the photoresist volume is determined. A development of the photoresist volume is calculated. The processor is used to produce a three-dimensional simulated scanning electron microscope image of the photoresist profile created by the development of the photoresist volume. The dimensional properties of the photoresist profile are measured.

9 Claims, 6 Drawing Sheets

Non-Transitory Computer Readable Medium With Instruction Modules Disposed Thereon
11

Fig. 6

PHOTORESIST SIMULATION

This application claims all rights and priority on prior pending U.S. provisional patent application Ser. No. 61/260,533 filed Nov. 12, 2009.

FIELD

This invention relates to the field of integrated circuit fabrication. More particularly, this invention relates to the simulation of a photoresist relief image as viewed and measured with a critical-dimension scanning electron microscope (CD-SEM).

BACKGROUND

Modeling strategies for optical lithography have typically applied the continuum approximation to the physics being simulated, meaning the use of continuous mathematics to describe the empirical observations. However, when reduced to a very small scale, the real world is discrete. For example, light energy within a very small volume is comprised of individual photons, and average light intensity is meaningless. Chemicals within a very small volume are comprised of individual molecules, and average chemical concentration is meaningless. Thus, the chemical and photo reactions within such small volumes are discrete and probabilistic—a reactant molecule or a photon might or might not be in a given position within the small volume for a reaction to occur.

As exposure doses decrease and resist dimensions shrink to less than about one hundred nanometers, stochastic resist effects and the effects of critical-dimension scanning electron microscopy upon the resist image become non-negligible.

What is needed, therefore, is a modeling method that overcomes problems such as those described above, at least in part.

SUMMARY

The above and other needs are met by a processor based method for measuring dimensional properties of a photoresist profile by determining a number acid generators and quenchers within a photoresist volume, determining a number of photons absorbed by the photoresist volume, determining a number of the acid generators converted to acid, determining a number of acid and quencher reactions within the photoresist volume, calculating a development of the photoresist volume, producing with the processor a three-dimensional simulated scanning electron microscope image of the photoresist profile created by the development of the photoresist volume, and measuring the dimensional properties of the photoresist profile.

In this manner, the effects of photo-acid generator loading, photo-acid generator absorbance, photo-acid generator quantum efficiency, quencher loading, photon shot noise, and so forth on the photoresist relief image can be studied, without having to perform multiple, expensive, and time-consuming empirical studies.

In various embodiments according to this aspect of the invention, the step of determining the number acid generators and quenchers within the photoresist volume comprises specifying a desired number of acid generators and specifying a desired number of quenchers based on a hypothetical photoresist formulation. In other embodiments the step of determining the number acid generators and quenchers within the photoresist volume comprises entering an actual number of acid generators and an actual number of quenchers based on an existing photoresist formulation. In some embodiments the step of determining the number of photons absorbed by the photoresist volume comprises specifying a desire number of photons based on a hypothetical exposure. In other embodiments the step of determining the number of photons absorbed by the photoresist volume comprises entering the number of photons based on a known exposure. In some embodiments the step of determining the number of the acid generators converted to acid comprises calculating the acid generators converted to acid via a photolysis mechanism In some embodiments the step of determining the number of the acid generators converted to acid comprises calculating the acid generators converted to acid via an ionization mechanism. In some embodiments the step of measuring the dimensional properties of the photoresist profile comprises measuring a hard-copy output of the three-dimensional simulated scanning electron microscope image with a ruler. In other embodiments the step of measuring the dimensional properties of the photoresist profile comprises mathematically evaluating a data file of the three-dimensional simulated scanning electron microscope image. Some embodiments include the step of fabricating integrated circuits using processes that are based at least in part on the dimensional properties of the photoresist profile.

According to another aspect of the invention there is described a processor based method for measuring dimensional properties of a photoresist profile by inputting photoresist and exposure parameters into a stochastic model of a photoresist process, computing the photoresist profile from the stochastic model using the processor, and measuring the dimensional properties of the photoresist profile using a CDSEM simulator running on the processor.

According to yet another aspect of the invention there is described a computer readable medium having instruction modules disposed thereon, where the instruction modules are not transitory signals, the instruction modules for instructing a processor to measure dimensional properties of a photoresist profile, the instruction modules operable for determining a number acid generators and quenchers within a photoresist volume, determining a number of photons absorbed by the photoresist volume, determining a number of the acid generators converted to acid, determining a number of acid and quencher reactions within the photoresist volume, calculating a development of the photoresist volume, producing with the processor a three-dimensional simulated scanning electron microscope image of the photoresist profile created by the development of the photoresist volume, and measuring the dimensional properties of the photoresist profile.

BRIEF DESCRIPTION OF THE DRAWINGS

Further advantages of the invention are apparent by reference to the detailed description when considered in conjunction with the figures, which are not to scale so as to more clearly show the details, wherein like reference numbers indicate like elements throughout the several views, and wherein:

FIG. 6 is a representation of a non-transitory computer readable medium with instruction modules disposed thereon, according to an embodiment of the present invention.

DETAILED DESCRIPTION

Figure 1:
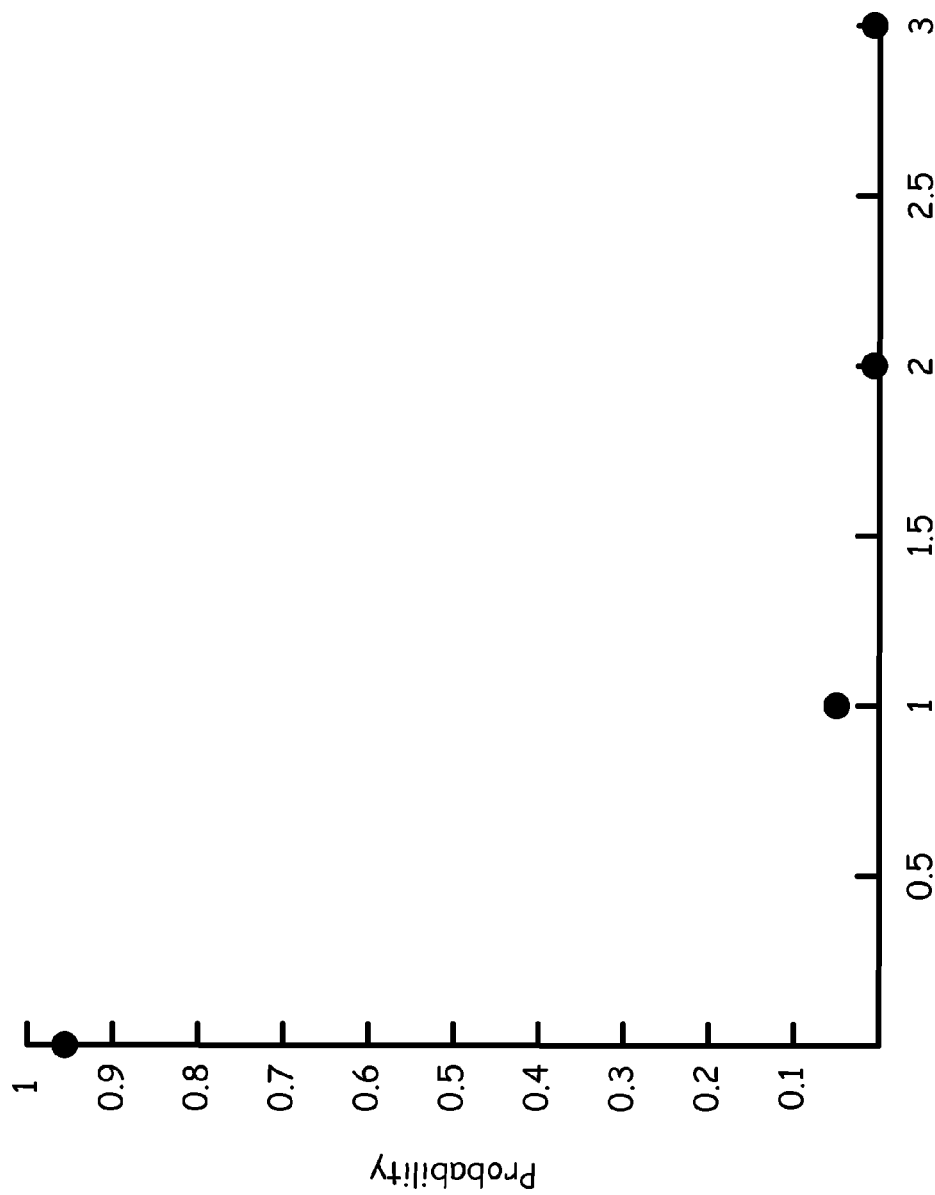
FIG. 1 is a chart depicting the probability of finding up to three photo-acid generators in a one cubic nanometer cell, according to an embodiment of the present invention.

Various embodiments of the present method enable important lithographic phenomena to be studied, such as:
1. Critical dimension uniformity,
2. Line-edge roughness, line-width roughness, and associated power versus frequency spectra,
3. Photon shot noise effects and uncertainty in receiving the expected dose,
4. Acid generation mechanisms, acid distribution, acid diffusivity, and associated effects on photoresist performance,
5. Photoacid generator loading, distribution, and effects on performance, and
6. Quencher loading, distribution, diffusion, and effects on performance.

Various embodiments of the present invention can be used to predict such statistical lithographic properties of a resist relief image as they would appear in actual CDSEM experiments. Various embodiments employ a combination of two simulation methods to produce a desired simulated result. The two methods that are combined include (1) a stochastic resist modeling method, and (2) a CDSEM image modeling method.

Generally, the stochastic resist modeling method simulates the physical-chemical formation of the resist relief image, such that several statistical lithographic properties of the relief image can be studied as a response of the input. The CDSEM image modeling method then processes the output of the stochastic resist model using a physical model that approximates the interaction of an electron beam with the relief image. The final output is a highly realistic—but simulated—image of the resist relief as it would be viewed and measured by an actual CDSEM.

Overview of the Stochastic Resist Model

The various methods for computer modeling of optical lithography processes usually follow a continuum approximation, which is the use of continuous mathematics to describe the average behavior. However, some events do not model well in a continuum domain, especially when considered in a very small volume. For example, light has a dual character in wave and quantum theory. The molecules that make up a photoresist layer are discrete. Chemical reactions are discrete and probabilistic. When describing behavior at length scales of tens of nanometers, an alternate approach to continuum modeling is to build the quantization of light and matter directly into the models, in what is called stochastic physical modeling, which uses probability distributions and random numbers to describe the statistical fluctuations that are expected.

This method allows a researcher to model lithographic conditions that cannot be modeled with a continuum model, such as line-width roughness (the fluctuation of the critical dimension along a resist line), line-edge roughness (the fluctuation of the placement of the resist line edge), critical dimension variability, critical shape variability, the probability of forming certain defects, and so forth.

This method also produces models that more closely approximate the formulation of actual resist. In this manner, the effects of photo-acid generator loading, photo-acid generator absorbance, photo-acid generator quantum efficiency, quencher loading, photon shot noise, and so forth on the photoresist relief image can be studied. Macro effects, such as the overall quantum yield of the exposure process can also be studied.

Stochastic resist modeling is more useful for critical dimensions that are no greater than about one hundred nanometers. Such critical dimensions are routinely encountered in ArF immersion lithography, ArF double-patterning lithography, and extreme ultraviolet lithography.

Description of the Stochastic Resist Model

The embodiments according to the present invention comprehend statistical fluctuations that occur during the exposure process, since the state of the acid image in the resist after exposure (the acid shot noise image) strongly influences later behavior of the photoresist relief, such as line width roughness, line edge roughness, critical dimension variability, contact hole circularity, and so forth.

Figure 5:
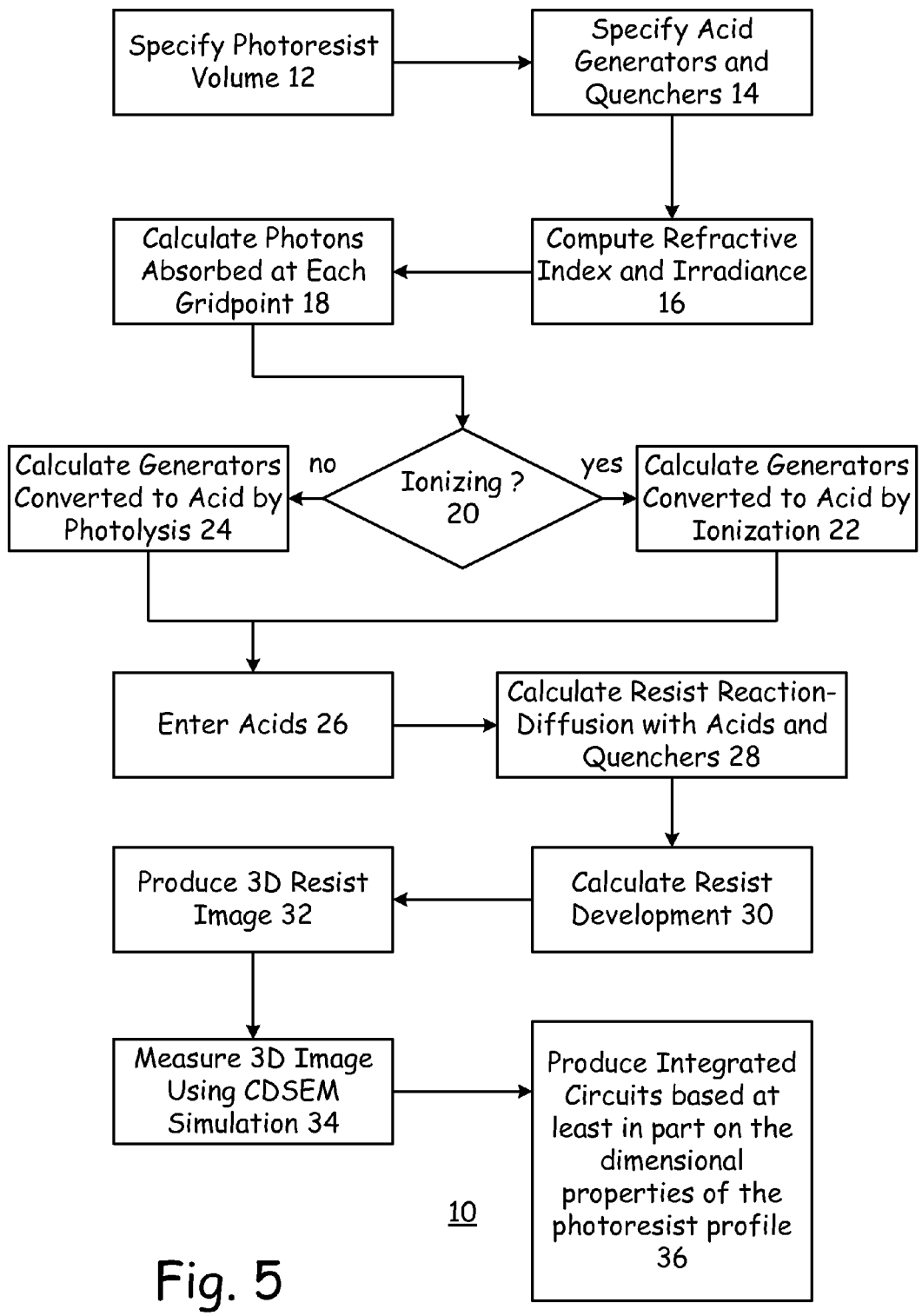
FIG. 5 is a flow chart for a method according to an embodiment of the present invention.

As depicted in the flow chart of one embodiment 10 of FIG. 5, the first step is to specify a desired building-block volume of photoresist, within which the basic computations will be performed, as given in block 12. Next, the number of acid generators and quenchers within this basic building-block volume are specified, as given in block 14. This number is dependent upon the type of photoresist that is to be modeled, and can reflect either an actual photoresist product, or a theoretical photoresist product. The refractive index and irradiance of the photoresist are computed or specified, as desired, as given in block 16. Again, these values can reflect either an actual photoresist product or a theoretical product.

The next step is to perform statistical computations on the number of absorbed photons, as given in block 18, because resists (specifically acid generators) are activated by the energy that is absorbed from the photons delivered during the exposure process. The average number of photons absorbed by a volume V with absorbance coefficient alpha is given by:

$$\bar{n} = \alpha (It) V \left( \frac{\lambda}{hc} \right)$$

where α is the absorbance of the photoresist, I is the intensity of the light used in the exposure, t is the exposure time, λ is the actinic wavelength, V is the volume of interest, c is the vacuum velocity of light, and h is Planck's constant. Thus, the average number of absorbed photons is proportional to wavelength, absorbance, dose (It) and volume. For example, about fourteen times more photons are absorbed during an ArF emission exposure, as compared to an extreme ultraviolet emission exposure, even though the absorbed dose is constant in the two examples.

The Poisson probability distribution can be used, for example, to model the counting statistics of the number of absorbed photons. The probability of observing k successful photon absorption events given the average number of absorbed photons is:

$$p(k; \bar{n}) = e^{-\bar{n}} \frac{\bar{n}^k}{k!}$$

The properties of the Poisson distribution include the fact that the variance of the distribution is equal to the mean:

$$\text{var } n = \bar{n}$$

and the standard deviation of the number of absorbed photons is equal to the square-root of the mean. The standard deviation of the number of absorbed photons is:

$$\sigma_n = \frac{\bar{n}}{\sqrt{\bar{n}}} = \frac{\sqrt{\bar{n}} \cdot \sqrt{\bar{n}}}{\sqrt{\bar{n}}} = \sqrt{\bar{n}}$$

The relative uncertainty of absorbing the expected number of photons (the expected dose) is:

$$\frac{\sigma_n}{\bar{n}} = \frac{1}{\sqrt{\bar{n}}}$$

This indicates that the relative uncertainty of observing the average number of absorbed photons rises as the average number of absorbed photons decreases—a phenomenon known as shot noise. For example, at ten millijoules per square centimeter and with an alpha of four per micron, the standard deviation of the number of absorbed photons with an ArF emission is about 1.7 times the mean number of absorbed photons. With an extreme ultraviolet emission, the standard deviation of the number of absorbed photons is about 6.4 times the mean number of absorbed photons.

The Poisson distribution can also be used to describe photoresist molecule counting statistics, such as the dispersion of discrete acid generators in a chemically-amplified resist film. FIG. 1 indicates the probability of finding n acid generators in a cubic volume having a size of one nanometer on a side when the acid generator loading is five percent of the resist solids. It is interesting to note that, in this example, ninety-five percent of all of the one cubic nanometer cells contain no photo-acid generators.

The individual acid generator molecules that are dispersed throughout a chemically-amplified photoresist layer are activated by absorbing energy from the photons received by the photoresist during exposure. The interaction of the generated acids with the resin polymer in the photoresist eventually produces soluble regions in the film, after processing the resist through a post-exposure bake and development in an aqueous base. Therefore, the statistics of the generated acids are of great importance to the properties of the resist relief image, because acids are the primary imprint of the optical projection image (the initial condition).

The stochastic resist models according to various embodiments of the present invention consider two probabilistic acid generator activation mechanisms. The first mechanism is direct photolysis, and the second mechanism is scattered low-energy electrons. A determination is made, as given in block 20, as to which mechanism is the more appropriate. If a photolysis mechanism is more appropriate, then the number of acid generators that are converted to acid by photolysis is calculated, as described below and given in block 24 of FIG. 5. If the ionization mechanism is more appropriate, then the number of acid generators that are converted to acid by ionization is calculated, as described below and given in block 22 of FIG. 5. In some embodiments both of the calculations are performed.

For the photolysis mechanism, the acid generators in the resist are activated by an absorbed photon with a probability that is equal to the quantum efficiency. At most, one acid is produced by the absorption of one photon. This is the most likely mechanism when the resist is irradiated by ArF light (wavelength of 193 nanometers). The distribution of the number of acids generated by direct photolysis and the effect upon the resist relief image is thus studied with stochastic resist simulation.

For the ionization mechanism, the acid generators are activated by scattered low-energy electrons. Similar to the photoelectric effect, low energy electrons can be produced by ionization of the resist upon absorbance of high-energy extreme ultraviolet photons. The energy deposited in the resist film can, in this manner, activate acid generators some distance from the photon absorption site. This is the most likely mechanism for acid generation upon irradiation by extreme ultraviolet light (wavelength of 13.5 nanometers). However, the distribution of the number of acids produced via ionization is somewhat less predictable than the direct photolysis mechanism, because the photoelectron exposure mechanism allows a single photon to generate multiple electrons, and each electron may then travel through the resist film, activating multiple acid generators. Therefore, more than one acid may be generated per photon absorption event.

In various embodiments, the ionization process is modeled as a two-step mechanism, and each step is a stochastic process. The probability of generating a specific number of acids is modeled as the product of a conditional probability:

$$P(n_{acid}|n_{photon})$$

with the probability of generating a specific number of photons given as:

$$P(n_{photon})$$

As described above, the probability for generating a photon is modeled with Poisson statistics. However, the overall probability of generating an acid is obtained by summing over all possible numbers of photons. Using a simple conditional probability statement, we can see that:

$$P(n_{acid}) = P(n_{acid}|n_{photon}) \cdot P(n_{photon})$$

and therefore, the generation of multiple acids is correlated with the absorption of a single photon. This correlation with the creation of multiple acid molecules violates a primary assumption for Poisson counting statistics and, therefore, the distribution of the number of acids that are generated by low energy photoelectrons is not a Poisson distribution. However, this complex distribution of the number of acids generated by ionization and electron scattering and their resultant effect upon the resist relief image can be studied with stochastic resist simulation.

Using one or both of these two activation methods, the number of acids is determined and entered into the mathematical model, as given in block 26. Once this is accomplished, the resist reactions between the acids and the quenchers in the photoresist are calculated, as given in block 28. This produces a model of the photoresist that indicates which portions of the photoresist have been exposed, and to what degree.

Next, the development of the photoresist is computed, as given in block 30. In this step, the effects of the developing solution upon the exposed portions of the photoresist, as previously calculated, are determined and entered into the model.

Once these steps have been accomplished, a three-dimensional graphical image of the photoresist can be produced, as given in block 32. It is appreciated that other steps in the mathematical model development, such as accounting for temperature, humidity, bakes, and other events are also included in the mode, as desired.

The image produced in step 32 looks just like a SEM image would, if a photograph were to be taken of an actual exposed and developed photoresist line pattern—including line edge and sidewall roughness, height variation, sidewall profile, overexposure, underexposure, and so forth. However, this image is produced mathematically instead of photographically—other than that, there are very few differences. But because an actual photoresist formulation does not have to be created, and actual processing conditions do not have to been applied to the process, a far greater number of conditions can be simulated in the present method, and in a shorter length of time, than in actual empirical studies.

Overview of the CDSEM Imaging Model

Because of their high quality, repeatability, and non-destructive nature, CDSEMs are the gold standard for the metrology of the features that are produced by optical lithography processes. A method that models the CDSEM's effects is clearly useful in producing a more realistic simulation.

Figure 2:
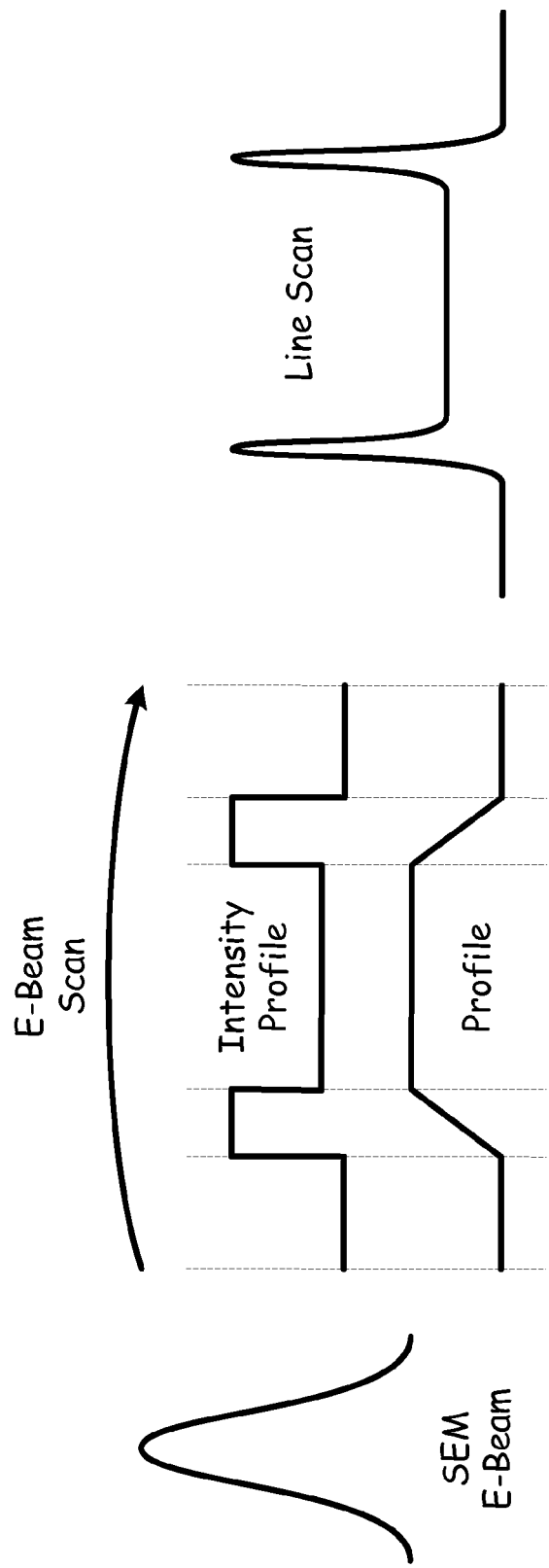
FIG. 2 graphically depicts the line scan that is created by scanning an electron beam across the profile of a feature such as a line of photoresist, according to an embodiment of the present invention.

Determining a critical dimension with a top-down scanning electron microscope begins with the creation of a line scan, or intensity signal from the secondary electron detector as the electron beam is scanned across the image. In practice, the line scan usually results from the averaging of several scans to reduce the noise in the signal. Once this is accomplished, a functional form is fit to the scan to make measurements between corresponding points, as depicted in FIG. 2.

An electron beam scans across the resist profile and secondary electrons that result from the interaction of the beam and material are collected in a detector. The secondary electrons come from a region that is typically no more than about five nanometers below the surface of the profile. Because the beam has a finite cross section, it illuminates a larger area on the profile side wall than on the horizontal surfaces, there is, therefore, a greater signal from the edges of the profile than from the center. If the beam were very thin and uniform, then the resulting intensity profile would appear quite square (ignoring extra electrons that escape from the corner regions of the profile). But because the beam actually has a Gaussian profile, the measured line scan appears as a convolution of the ideal square intensity profile with the Gaussian kernel.

Figure 3:
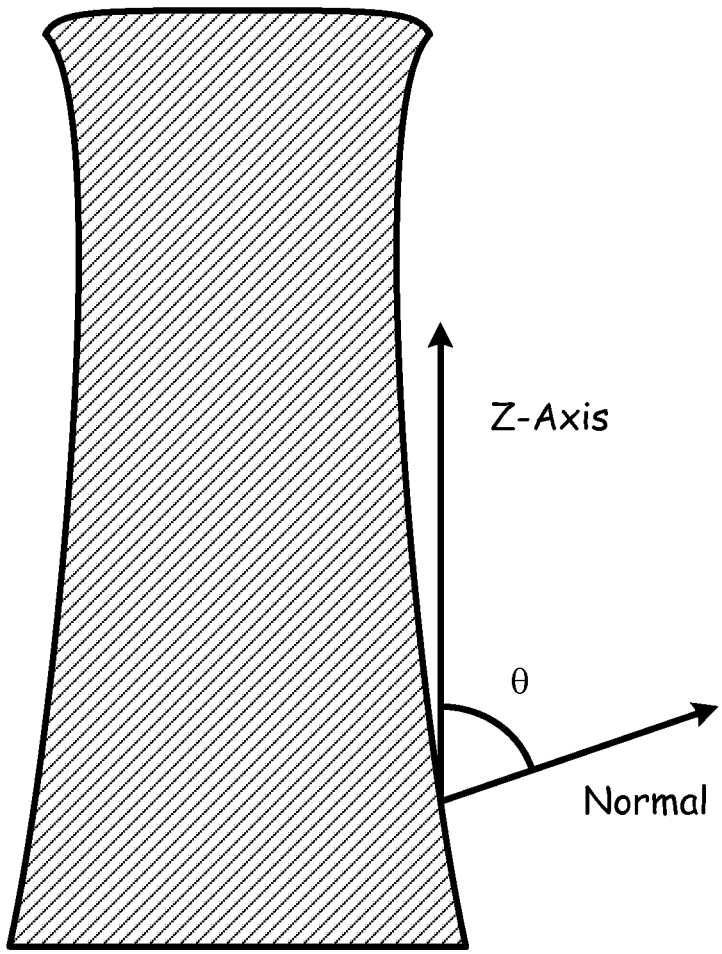
FIG. 3 depicts the Z axis and normal lines as oriented by the sidewall of a feature such as a line of photoresist, according to an embodiment of the present invention.

The simplest physical model that attains the goal of producing a better match to experiment than a constant offset is used. The starting point is noting that the intensity profile is a function of the angle between the surface normal and the z-axis, as depicted in FIG. 3. This function is at a maximum for vertical sidewalls (sidewall angle θ of ninety degrees) and a minimum for horizontal sidewalls (sidewall angle θ of zero degrees). The secant function can be used to model the intensity of the secondary electron signal:

$$I \propto \frac{1}{\cos\theta}$$

The secant function produces its minimum values for small angles, and ramps up to its maximum values for angles near ninety degrees.

However, the sine function has a better behavior for nearly vertical sidewalls. The sine function is similar, though gentler in its rise toward its maximum value, resulting in a wider peak centered over the sidewalls. Note that the differences between these two distributions can be virtually scaled away in the final step. In addition to the angular dependence, the intensity can be adjusted to account for the fact that the resist material generally returns slightly more secondary electrons than the substrate, by simply changing the constant of proportionality for resist material and other materials. In other words, a constant offset is added to the intensity for portions of the curve that are covered by resist material. The final form of the intensity profile function is:

$$I \propto A\sin\theta + B\delta_R(\vec{x})$$

where:

$$\delta_R(\vec{x}) = \begin{cases} 1 & \text{if the position } \vec{x} \text{ is covered with resist} \\ 0 & \text{otherwise} \end{cases}$$

Figure 4:
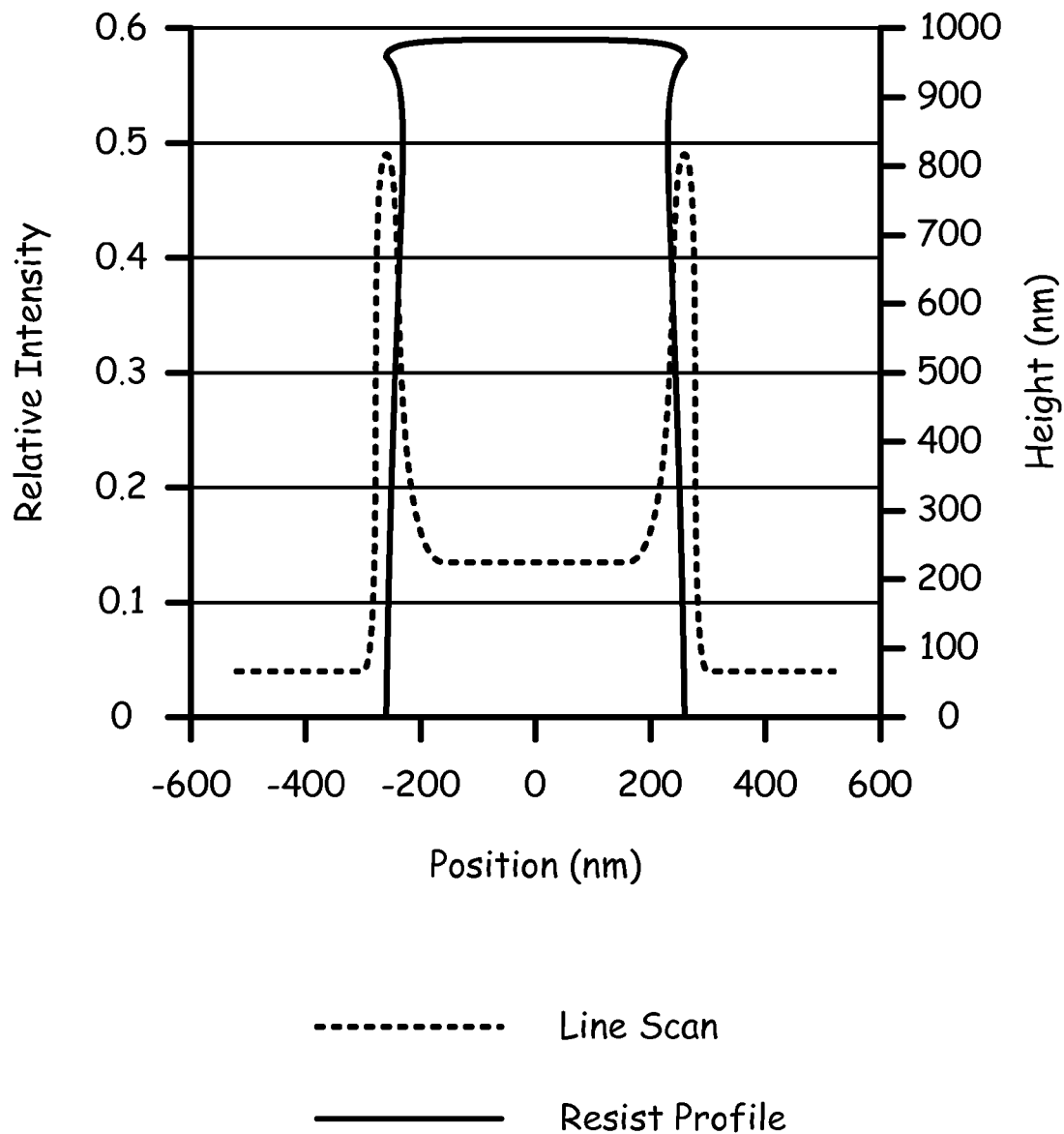
FIG. 4 depicts a simulated line scan according to an embodiment of the present invention.

A convolution of the ideal intensity profile is performed with a Gaussian kernel to arrive at a final simulated line scan, as depicted in FIG. 4. Adjusting the width of this Gaussian profile gives the desired scaling to the intensity profile mentioned above. The CDSEM metrology method is applied to the line scan to produce a critical dimension value, as given in block 34 of FIG. 5. In some embodiments, only the mid critical dimension value is produced in the data that is produced. In some embodiments, integrated circuits are fabricated using processes that are based at least in part on the dimensional properties of the photoresist profile, as given in step 36.

Thus, various embodiments of the invention produce computer simulations of the resist relief image with a high degree of detail. Computer models of several statistical effects can be produced, such as line width roughness, line edge roughness, critical dimension variability, contact hole circularity—all as viewed and measured by the CDSEM. Computer modeling of certain forms of defectivity in the resist relief image are also possible. These embodiments enable scientists to replace costly empirical studies with less-expensive, highly-realistic, computer models.

Some of these method embodiments are performed on processor-based equipment, such as personal computers or more specialized graphic processing computers. Some of these embodiments include a non-transitory computer readable medium having instruction modules disposed thereon, as depicted in FIG. 6. When the instruction modules are executed by a processor, they instruct the processor to measure the dimensional properties of a simulated photoresist profile. The output of these embodiments includes the graphical images of the photoresist profile and the tabulated critical dimension data in regard to the simulated SEM images. This information is used by process engineers and others to accomplish a number of different objectives as described elsewhere herein, and also including general objectives such as developing new photoresists, developing processing recipes, and performing initial qualification of photoresists and processes. Such information eventually leads to the processing of actual integrated circuits and other structures.

The foregoing description of embodiments for this invention has been presented for purposes of illustration and description. It is not intended to be exhaustive or to limit the invention to the precise form disclosed. Obvious modifications or variations are possible in light of the above teachings. The embodiments are chosen and described in an effort to provide illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A non-transitory computer readable medium having instruction modules disposed thereon, the instruction modules, when executed by a processor, for instructing the processor to measure dimensional properties of a simulated photoresist profile, the instruction modules performing steps of:
   determining a number acid generators and quenchers within a virtual photoresist volume;
   determining a number of photons absorbed by the virtual photoresist volume;
   determining a number of the acid generators converted to acid within the virtual photoresist volume;
   determining a number of acid and quencher reactions within the virtual photoresist volume;
   calculating a development of the virtual photoresist volume;
   producing with the processor a three-dimensional simulated scanning electron microscope image of the simulated photoresist profile created by the development of the virtual photoresist volume;
   measuring the dimensional properties of the simulated photoresist profile; and
   specifying processes for fabricating integrated circuits based at least on the dimensional properties of the photoresist profile.

2. The non-transitory computer readable medium of claim 1, wherein the instruction modules to perform the step of determining the number of acid generators and quenchers within the photoresist volume comprises specifying a desired number of acid generators and specifying a desired number of quenchers based on a hypothetical photoresist formulation.

3. The non-transitory computer readable medium of claim 1, wherein the instruction modules to perform the step of determining the number of acid generators and quenchers within the photoresist volume comprises entering an actual number of acid generators and an actual number of quenchers based on an existing photoresist formulation.

4. The non-transitory computer readable medium of claim 1, wherein the instruction modules to perform the step of determining the number of photons absorbed by the photoresist volume comprises specifying a desired number of photons based on a hypothetical exposure.

5. The non-transitory computer readable medium of claim 1, wherein the instruction modules to perform the step of determining the number of photons absorbed by the photoresist volume comprises entering the number of photons based on a known exposure.

6. The non-transitory computer readable medium of claim 1, wherein the instruction modules to perform the step of determining the number of the acid generators converted to acid comprises calculating the acid generators converted to acid via a photolysis mechanism.

7. The non-transitory computer readable medium of claim 1, wherein the instruction modules to perform the step of determining the number of the acid generators converted to acid comprises calculating the acid generators converted to acid via an ionization mechanism.

8. The non-transitory computer readable medium of claim 1, wherein the instruction modules to perform the step of measuring the dimensional properties of the photoresist profile comprises measuring a hard-copy output of the three-dimensional simulated scanning electron microscope image with a ruler.

9. The non-transitory computer readable medium of claim 1, wherein the instruction modules to perform the step of measuring the dimensional properties of the photoresist profile comprises mathematically evaluating a data file of the three-dimensional simulated scanning electron microscope image.

* * * * *